(12) United States Patent
Schie (10) Patent No.: US 11,883,167 B2
(45) Date of Patent: *Jan. 30, 2024

(54) DEVICE TO EXTRACT PHYSIOLOGICAL INFORMATION AND METHOD THEREFOR

(71) Applicant: David Schie, Houston, TX (US)

(72) Inventor: David Schie, Houston, TX (US)

( * ) Notice: Subject to any disclaimer, the term of this patent is extended or adjusted under 35 U.S.C. 154(b) by 242 days.

This patent is subject to a terminal disclaimer.

(21) Appl. No.: 17/188,146

(22) Filed: Mar. 1, 2021

(65) Prior Publication Data

US 2021/0244323 A1 Aug. 12, 2021

Related U.S. Application Data

(63) Continuation of application No. 15/895,401, filed on Feb. 13, 2018, now Pat. No. 10,973,446.

(60) Provisional application No. 62/458,465, filed on Feb. 13, 2017.

(51) Int. Cl.
| | |
|---|---|
| *A61B 5/1455* | (2006.01) |
| *A61B 5/026* | (2006.01) |
| *A61B 5/00* | (2006.01) |
| *G01N 33/49* | (2006.01) |
| *A61B 5/0205* | (2006.01) |
| *H01S 5/02345* | (2021.01) |
| *G02C 11/00* | (2006.01) |
| *H01S 5/00* | (2006.01) |
| *A61B 5/024* | (2006.01) |
| *A61B 5/145* | (2006.01) |

(52) U.S. Cl.
CPC ........ *A61B 5/14552* (2013.01); *A61B 5/0205* (2013.01); *A61B 5/0261* (2013.01); *A61B 5/4845* (2013.01); *A61B 5/6803* (2013.01); *A61B 5/726* (2013.01); *A61B 5/7207* (2013.01); *A61B 5/7267* (2013.01); *A61B 5/7278* (2013.01); *G01N 33/49* (2013.01); *H01S 5/02345* (2021.01); *A61B 5/02427* (2013.01); *A61B 5/14532* (2013.01); *A61B 5/14546* (2013.01); *A61B 2562/0238* (2013.01); *G02C 11/10* (2013.01); *H01S 5/0071* (2013.01)

(58) Field of Classification Search
CPC ... A61B 5/1455; A61B 5/6803; A61B 5/4845; A61B 5/0205
See application file for complete search history.

(56) References Cited

U.S. PATENT DOCUMENTS

| | | | |
|---|---|---|---|
| 10,307,085 B2* | 6/2019 | Sales | A61B 5/318 |
| 2006/0022761 A1* | 2/2006 | Abeles | G04F 5/14 |
| | | | 331/94.1 |
| 2010/0081901 A1* | 4/2010 | Buice | A61B 5/6838 |
| | | | 600/324 |
| 2015/0057511 A1* | 2/2015 | Basu | A61B 5/6826 |
| | | | 600/475 |
| 2015/0245782 A1* | 9/2015 | Morland | A61B 5/0095 |
| | | | 600/301 |
| 2016/0216777 A1* | 7/2016 | Geiger | G06F 3/0312 |
| 2018/0145205 A1* | 5/2018 | Chen | A61B 5/14552 |

* cited by examiner

*Primary Examiner* — Marjan Fardanesh
(74) *Attorney, Agent, or Firm* — Weiss & Moy, PC; Jeffrey D. Moy (57) ABSTRACT

A device to extract physiological information has at least one laser emitter. At least one optical detector is used to detect a change in optical power absorption. The laser emitter and optical detector are wire bonded into a chip scale module.

21 Claims, 10 Drawing Sheets

DEVICE TO EXTRACT PHYSIOLOGICAL INFORMATION AND METHOD THEREFOR

RELATED APPLICATIONS

This patent application is related to U.S. Provisional Application No. 62/458,465 filed Feb. 13, 2017, entitled "HEART WAVEFORM & BLOOD ALCOHOL EXTRACTION FROM A DISTANCE" in the name of the same inventor, and which is incorporated herein by reference in its entirety. The present patent application claims the benefit under 35 U.S.C § 119(e).

TECHNICAL FIELD

The present application relates generally to the technical field of medical and wearable devices, and more specifically, to the technical field of a device using laser emitters to extract physiological information from a user.

BACKGROUND

Many medical and/or wearable devices utilize optical means coupled to the skin to extract physiological information from a living subject. For example, a fitness tracker utilizes the change in optical power as light absorption varies with blood flow through arteries and veins. Heart rate information is then used to measure stress (HRV), fatigue, activities or illness. Similar means exist to determine other factors such as oxygenation, blood alcohol content, glucose, keytones, and the like.

Many medical and wearable devices utilize optical emitters and optical detectors such as photodetectors as the optical means to extract physiological information. Unfortunately, these types of devices have historically had several significant problems. Medical and wearable devices utilizing optical emitters and optical detectors generally do not work more than 1-2 mm away from the skin or the wearer. Further, optical detectors such as photodetectors are easily saturated by side light. For example, when theyare moved away from the skin of the wearer, side light may be detected by the photodetectors rather than just the reflected light. As a result the photodetectors may saturate or have a limited operation range,. To overcome this the optical emitters must be physically and optically separated by a barrier from the optical detector resulting in a much larger surface area for the assembly and the photodetector kept close to the skin to ensure light from the outside environment and side light from emitters is blocked.

Another issue is that medical and wearable devices generally use light emitting diode emitters. The light emitting diodes generate widely scattered light requiring optics that force deep recessing of 5 mm or more into typical form factors and often external lensing. However, the light emitting diodes do not elicit reflections from more than 1-2 mm away strong enough to measure. Thus, the result is that bands or watches which extract information like heart rate using light emitting diodes have to be pulled very tight against the skin of the wearer and form factors such as jewelry or glasses are not compatible with these types of emitter/detector systems. Additionally, form factors such as glasses are not possible because head shapes variation is too great to ensure that the light emitted from the light emitting diodes will reflect back into the detector from the skin once distance starts to exceed 1-2 mm, non-withstanding the risk of saturation by side light.

Therefore, it would be desirable to provide a system and method that overcomes the above.

SUMMARY

In accordance with one embodiment, a device to extract physiological information is disclosed. The device has at least one laser emitter. At least one optical detector is provided to detect a change in optical power absorption. The at least one laser emitter and the at least one optical detector are wire bonded into a chip scale module.

In accordance with one embodiment, a device to extract physiological information is disclosed. The device has a processor. At least one laser emitter is coupled to the processor. At least one optical detector detects a change in optical power absorption and is coupled to the processor. A passive optical device directs light beams from the at least one laser. A lenslet collimates and directs the light beams from the one or more laser emitters at one or more different angles.

In accordance with one embodiment, a device to extract blood chemistry information is disclosed. The device has a means by which to measure light in the approximately 9.5 um and 10.4 um range and emitters all of which may be tunable. An example is a 9.5 um QCL and a 10.4 um DFB QCL emitter. Detectors may be a HgCdTe photodetector or a tunable detector such as a MOEMS fabry-perot interferometer. The at least one detector detects at least one of thermal infrared waves or radiation resulting from excitation by the 9.5 um QCL and a 10.4 um DFB QCL. Differences in the measurements may be used to measure alcohol, glucose/glucogens, keytones or other blood chemistry.

BRIEF DESCRIPTION OF THE DRAWINGS

The present application is further detailed with respect to the following drawings. These figures are not intended to limit the scope of the present application but rather illustrate certain attributes thereof. The same reference numbers will be used throughout the drawings to refer to the same or like parts.

FIG. 7 is an exemplary device placed within a glasses frame in accordance with one aspect of the present invention; a FIG. 9 is an exemplary device placed within a watch band/bracelet in accordance with one aspect of the present invention;

DESCRIPTION OF THE APPLICATION

The description set forth below in connection with the appended drawings is intended as a description of presently preferred embodiments of the disclosure and is not intended to represent the only forms in which the present disclosure can be constructed and/or utilized. The description sets forth the functions and the sequence of steps for constructing and operating the disclosure in connection with the illustrated embodiments. It is to be understood, however, that the same or equivalent functions and sequences can be accomplished by different embodiments that are also intended to be encompassed within the spirit and scope of this disclosure.

The present disclosure discloses a device to extract physiological information from a user which utilizes laser emitters instead of light emitting diodes. The device may contain various other components to direct the light from the laser emitters and to send multiple beam angles out to ensure some of the beams will reflect back into the detector.

Figure 1:
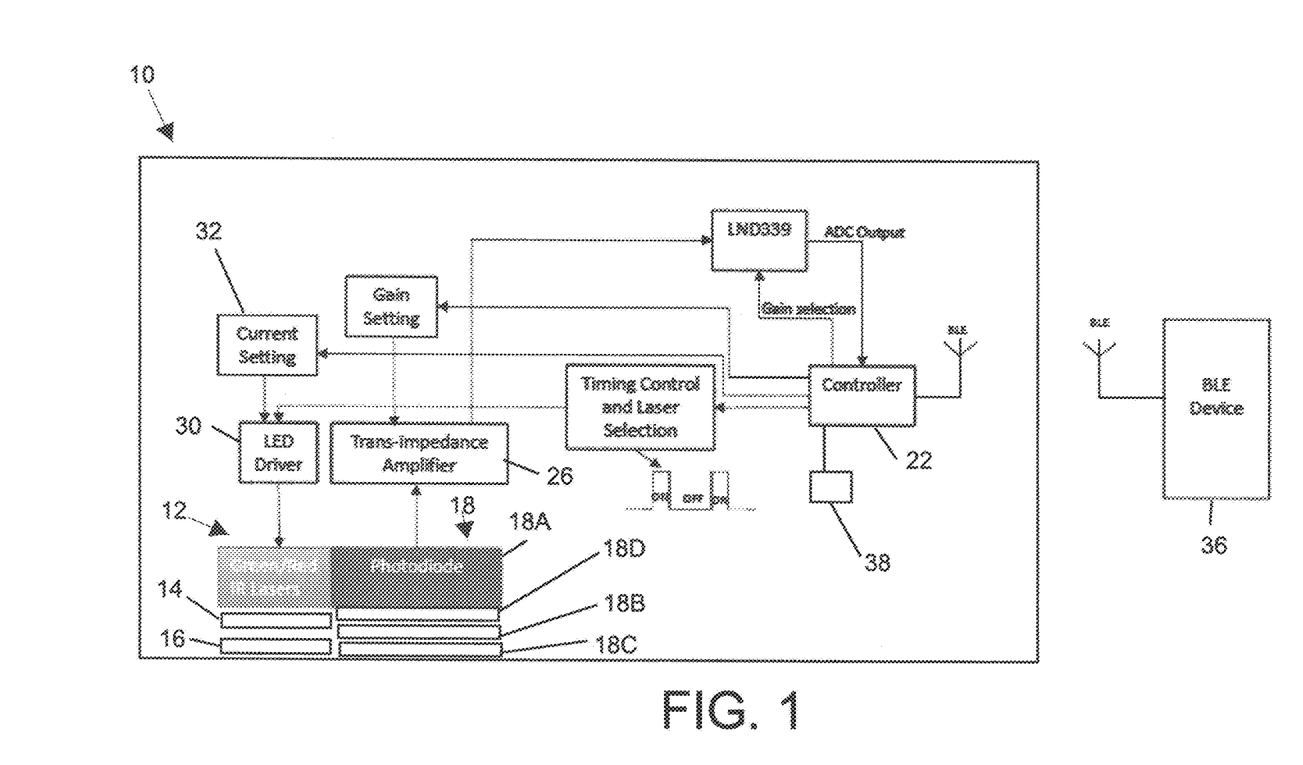
FIG. 1 is an exemplary block diagram of device to extract physiological information from a user in accordance with one aspect of the present application.
Figure 2:
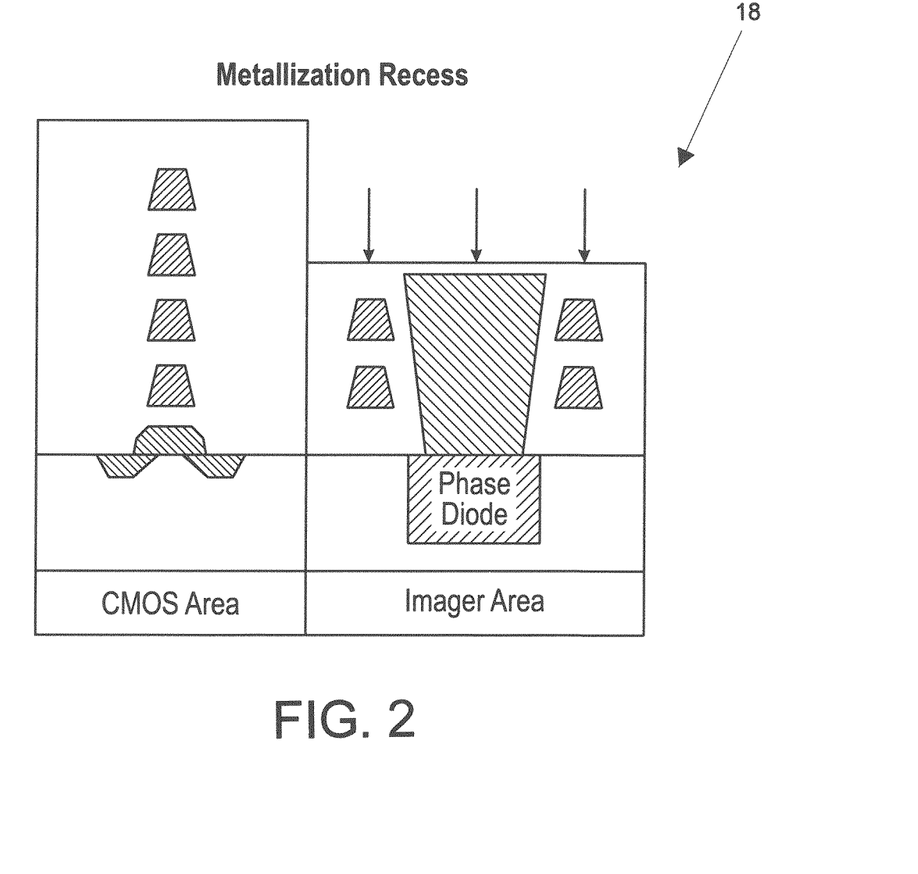
FIG. 2 is an exemplary device to extract physiological information from a user in accordance with one aspect of the present application.

Referring to FIGS., a device 10 to extract physiological information from a user is shown. The device 10 uses laser emitters 12 instead of light emitting diodes. The laser emitters 12 may emit a green laser, infrared laser or the like. The laser emitters 12 may be Quantum Cascade Lasers (QCL), distributed feedback (DFB) laser or the like including tunable lasers. In accordance with one embodiment, a 9.5 um Fabry-Perot QCL or equivalent wavelength and a 10.4 um DFB QCL or equivalent wavelength are used. The laser emitters 12 may be a vertical-cavity surface-emitting laser (VCSEL) 12A. VCSELs 12A are a type of semiconductor laser diode where light beam emission is perpendicular to the surface of the wafer. Alternately, or in addition to, the laser emitter 12 may be a side emitting laser 12B where the light beam may emit from surfaces formed by cleaving the individual chip out of a wafer such as a side emitting green laser or the like. The laser emitter 12 maintain a much tighter beam compared to LEDs and thus may be used at greater distances than LEDs. In general, the laser emitter 12 may be an array of laser emitters 12C as shown in FIG. 2. In accordance with one embodiment, the laser emitters 12 may be tunable laser emitters whose wavelength of operation may be tunable over a desired wavelength range. Similarly, the detectors may be tunable detectors whose wavelength of operation may be tunable over a desired wavelength range.

Figure 5:
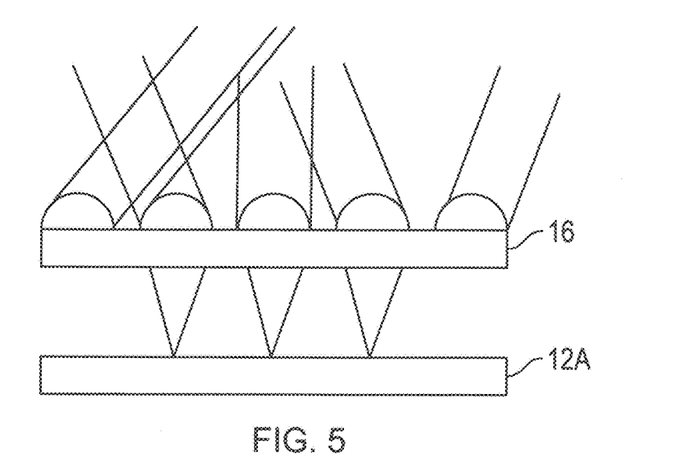
FIG. 5 is an exemplary lenslet used in the device in accordance with one aspect of the present invention.

The laser emitters 12 may be coupled to a passive optical component 14. The passive optical component 14 may be used to direct the light beam emitted by the laser emitters 12. The passive optical component 14 may be devices such as a prism, cylinders, mirrors or similar devices used to direct light beams. The laser emitters 12 may be coupled to a lenslet 16. The lenslet 16 is an array of small lenses located in the same plane. The lenslet 16 may be used to collimate the light beam emitted by the laser emitter 12 and to send out multiple light beam angles out to ensure some of the light beams will reflect back into a detector 18 by the topologies of many different temples, wrists, chests or other skin areas as may be seen in FIG. 5.

By having the laser emitters 12 illuminate the skin of the user, the detector 18 can measure changes over time in the optical power of the light beam reflected back which provides information such as photoplethysmogram heart information. Alternatively, a processor may measure differences in the amount of light absorbed at different wavelengths. For example alcohol content in blood may be measured by the difference between light absorbed at 9.5 um vs that at 10.4 um. A processor 22 may then be able to analyze this information to extract physiological information from the user. The processor 22 may calculate the change in optical power as light absorption varies with blood flow or excitation frequency through arteries and veins to monitor changes in blood flow, heart rate, oxygenation, blood alcohol content and the like. The processor 22 may use wavelet processing and machine learning to extract signals of interest from noise and motion artifacts without the disadvantages of frequency based filtering which tend to damage the signal of interest and struggle to separate other physiological sources such as EMG or movement (see FIG. 5A-6). The processor 22 may have a transmitter 34. The transmitter 34 may be used to wirelessly transmit data from the device 10 to a device 36. The device 36 may be used to read and display the data collected and calculated by the device 10. The device 36 may be a smartphone, tablet or similar device. In accordance with one embodiment, Bluetooth standards may be used for transmitting the data from the device 10. The device 10 may have a power source 38. The power source 38 may be a battery or the like used to power the non-passive devices.

To allow the laser emitters 12 to be placed in close proximity and without optical separation the device 10 uses a photodetector 18A as the detector 18. The photodetector 18 may be silicon detector, an HgCdTe photodetector or tunable IR filter detector such as a Micro-Opto-Electromechanical System (MOEMS) fabry-perot interferometer. HgCdTe or mercury cadmium telluride is useful for infrared detection because of: (1) Adjustable bandgap from 0.7 to 25 µm; (2) Direct bandgap with high absorption coefficient; (3) Moderate dielectric constant/index of refraction, (4) Moderate thermal coefficient of expansion and (5) Availability of wide bandgap lattice-matched substrates for epitaxial growth.

The photodetector 18A is configured to block side light. The photodetector 18A may include on chip side light blocking 18B, light pipe 18C, anti-glare/anti-refraction coating 18D, on chip lensing and other means to reduce the incidence of side light being gathered and to reduce distortion. Side light blocking 18B may be edging or the like formed around the photodetector 18A to prevent side light from entering the photodetector 18A, light pipes which only allow light vertically to fall upon a photodetector, one or two layers of on chip lensing and anti-glare/anti-refraction coating.

Figure 6A:
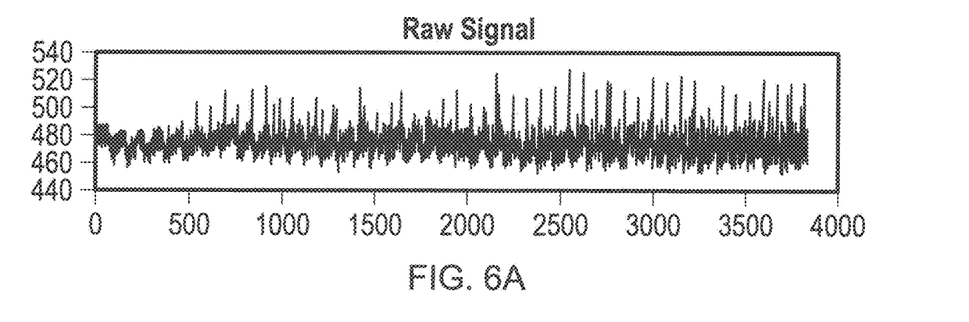
FIG. 6A-6B show reflected light signals received by the device in accordance with one aspect of the present invention.
Figure 6B:
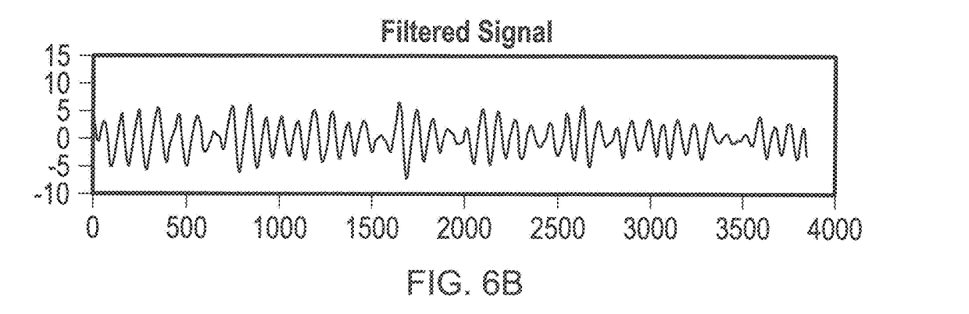
Figure 7:
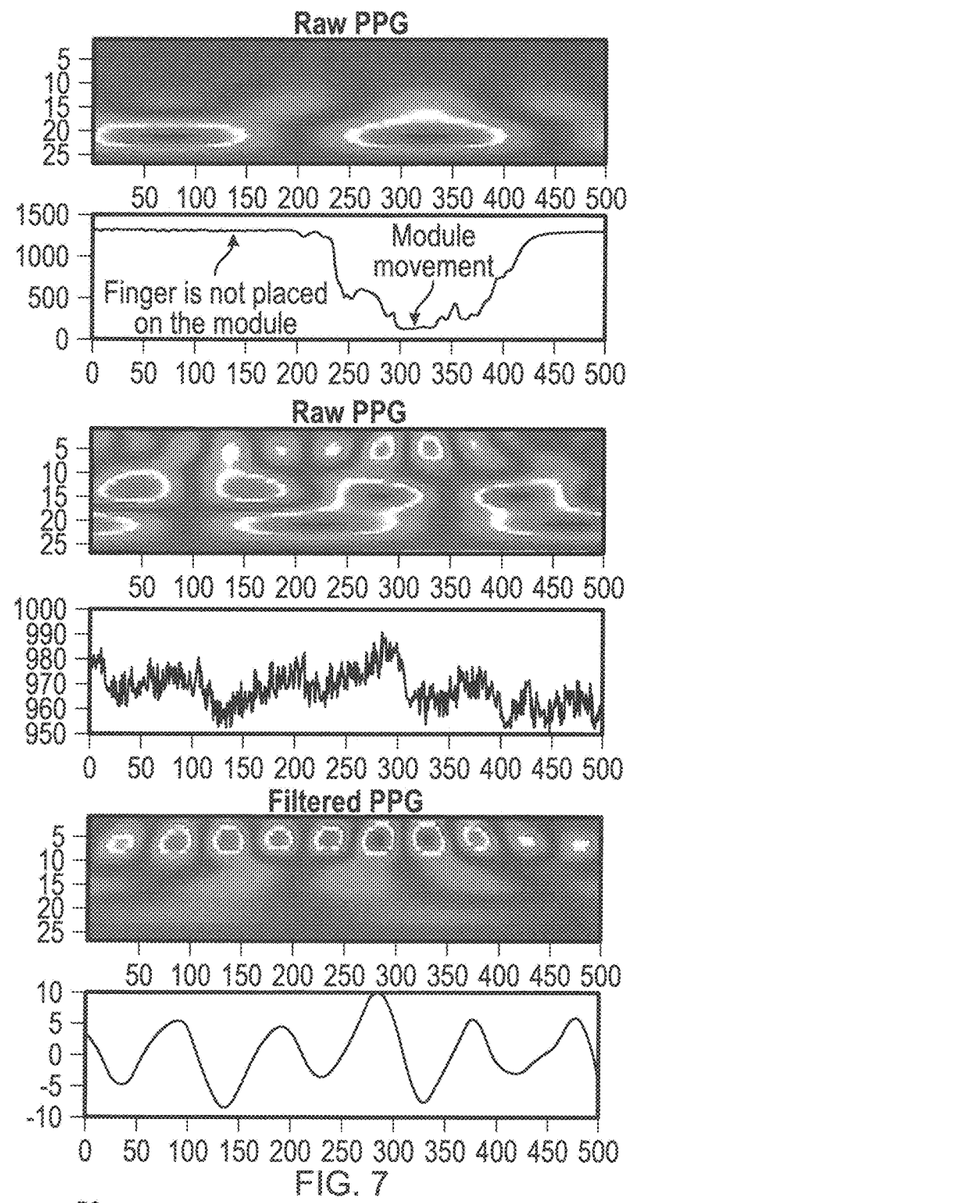
FIG. 7 shows wavelet processed reflected light wave signals including motion artifact rejection in accordance with one aspect of the present invention.

Using the above, the device 10 may be utilized more than 1-2 mm from the skin without saturating. FIG. 6A-6B, show the reflected light signal received when the device 10 is 7 mm away from the skin of the user. FIG. 6A show the raw light signal reflected back to the device 10 while FIG. 6B shows the extracted filtered signal. As one can see, even at 7 mm away, the device 10 is able to receive and read the reflected light signal.

Figure 8:
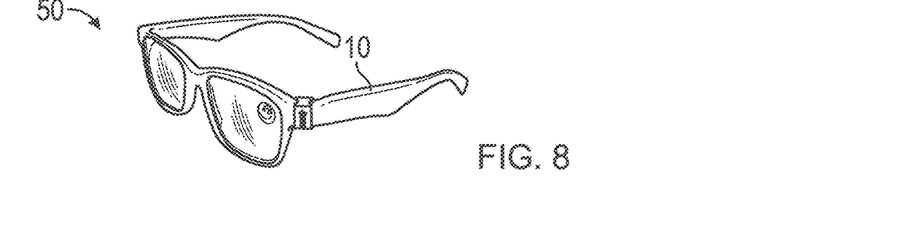
Figure 9:
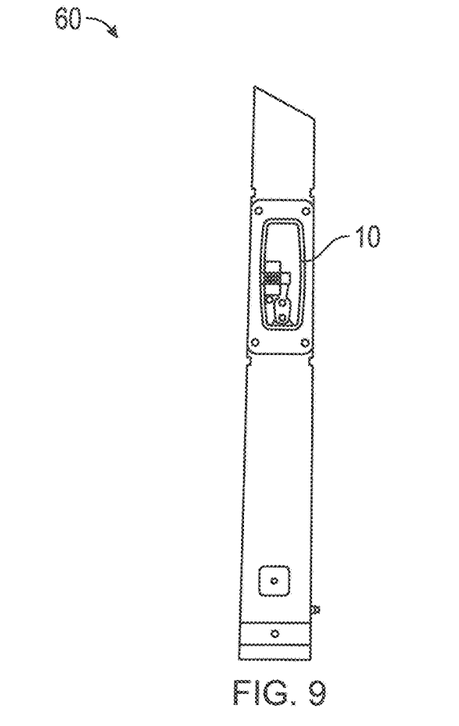
Figure 10:
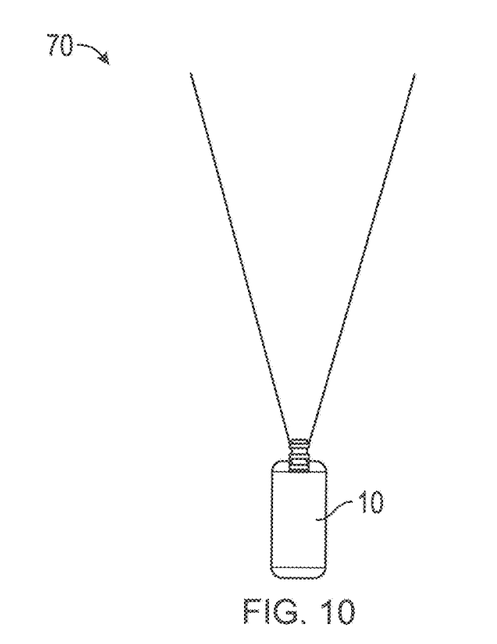
FIG. 10 is an exemplary device placed within a piece of jewelry in accordance with one aspect of the present invention.
Figure 11:
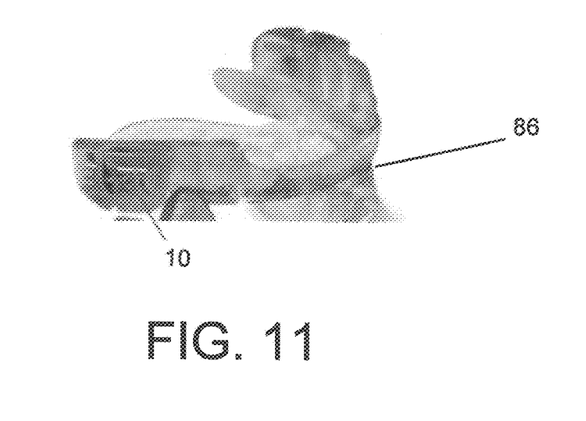
FIG. 11 is an exemplary device placed within an oral appliance in accordance with one aspect of the present invention.

By being able to receive the reflected light signal from greater distances, the device 10 may be used in different form factors and applications. For example, the device may allow uses such as, but not limited to: i) glasses 50 measuring heart rate or creating a photoplethysmogram (PPG), blood alcohol, glucose and glucogens, peripheral capillary oxygen saturation (SPO2), ketones, respiration, diet, and the like from the temple of a user as shown in FIG. 8; ii) bands/watches 60 which may be worn loosely FIG. 8; iii) jewelry such as necklaces 70 (FIG. 10), rings or ear rings which may be worn loosely and require small electronic assembles; iv) clothing and apparel which may be worn loosely; v) information may be extracted from within the mouth by coupling to an oral appliance 80 as shown in FIG. 10; vi) skin cancer may be detected using measured optical information compared against a database of such information from by a machine learning algorithm; and vii) compatibility of a person's skin with different cosmetics may be provided by comparing the optical information compared against a database of optical information favoring different cosmetic products by a machine learning algorithm; vii) optical detectors focused on the UV bands can measure and time the hazards of damaging sun exposure; viii) in combination with these optical detectors an ECG detector elsewhere on the body may be combined with the optical information to measure pulse wave velocity, arterial stiffness and these may be converted into blood pressure; ix) cardiac and capillary based authentication or identification information may be extracted. By taking the time between the electrical ECG peak current and the fastest derivative of the PPG waveform (the time the heart pushes the blood to the time it arrives and dividing by the distance from the heart to the point of measurement, we get Pulse Wave Velocity (PWV). PWV is the velocity at which the arterial pulse propagates through the circulatory system. PWV may be used as a measure of arterial stiffness and may have a correlation with cardiovascular events and an indicator of target organ damage.

Figure 3:
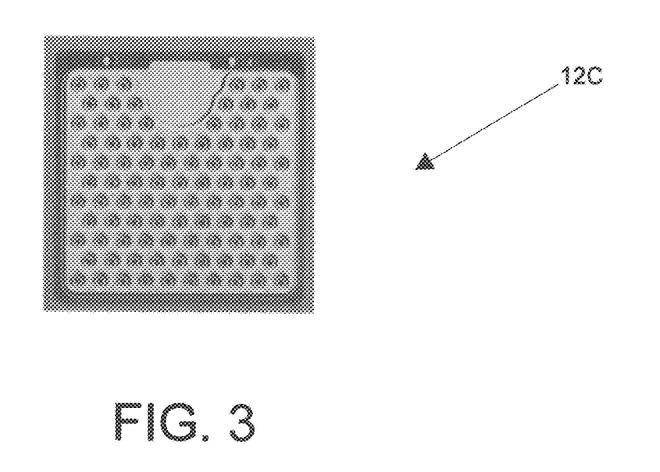
FIG. 3 is an exemplary laser emitter array used in the device in accordance with one aspect of the present invention.
Figure 4:
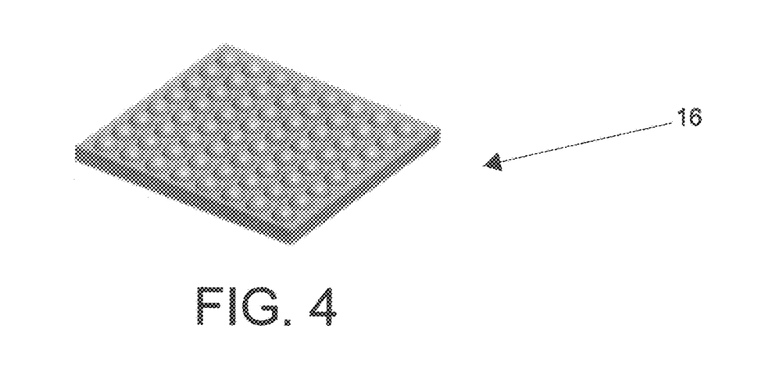
FIG. 4 is an exemplary lenslet used in the device in accordance with one aspect of the present invention.

As may be seen in FIG. 2, to further reduce size of the device 10 a hybrid substrate and wire bonding techniques may be used where the laser emitters 12, passive optical component 14, processor 22 and other components may be wire bonded directly to the substrate to avoid typical plastic, ceramic or plastic packaging area spacings. Using these techniques, modules of significantly less than 5 mm thick and less than 3×3 mm in surface area may be constructed. The use of laser emitters 12 may allows very thin packaging by eliminating the optics normally required by LEDs. Laser emitters 12 such as IR VCSELs 12A for example are available with multiple emitters as shown in FIG. 3 which might emit a +/−17° beam which may be collimated by the lenslet 16 designed to interface to a multi-element laser die.

By creating device 10 using wire bond techniques, typical called chip scale modules or multi-chip modules, with the side light blocking photodetector 18A and placing the laser emitters 12 next to the detector 18 it is possible to minimize module size compared with solutions which must separate emitters from the detector, and to make thinner modules compared to those utilizing LED emitters. These modules may use "glob top" opaque materials to block light over active components such as transconductors, op-amps, gain devices or multiplexers and the entire assembly may be encapsulated by a transparent coating material for mechanical resilience and waterproofing or optical components may be "glob topped" with a transparent coating. Additionally, physiological information can be extracted from more than 1-2 mm away from the module. Combining this with a processor 22 capable of processing wavelet and other information allows extraction during motion and in real world environments where noise is present. Finally, coupling the device 10 to a portable form factor such a band or glasses and operating them from a battery allows the device 10 to be widely and convenient to used.

Figure 12:
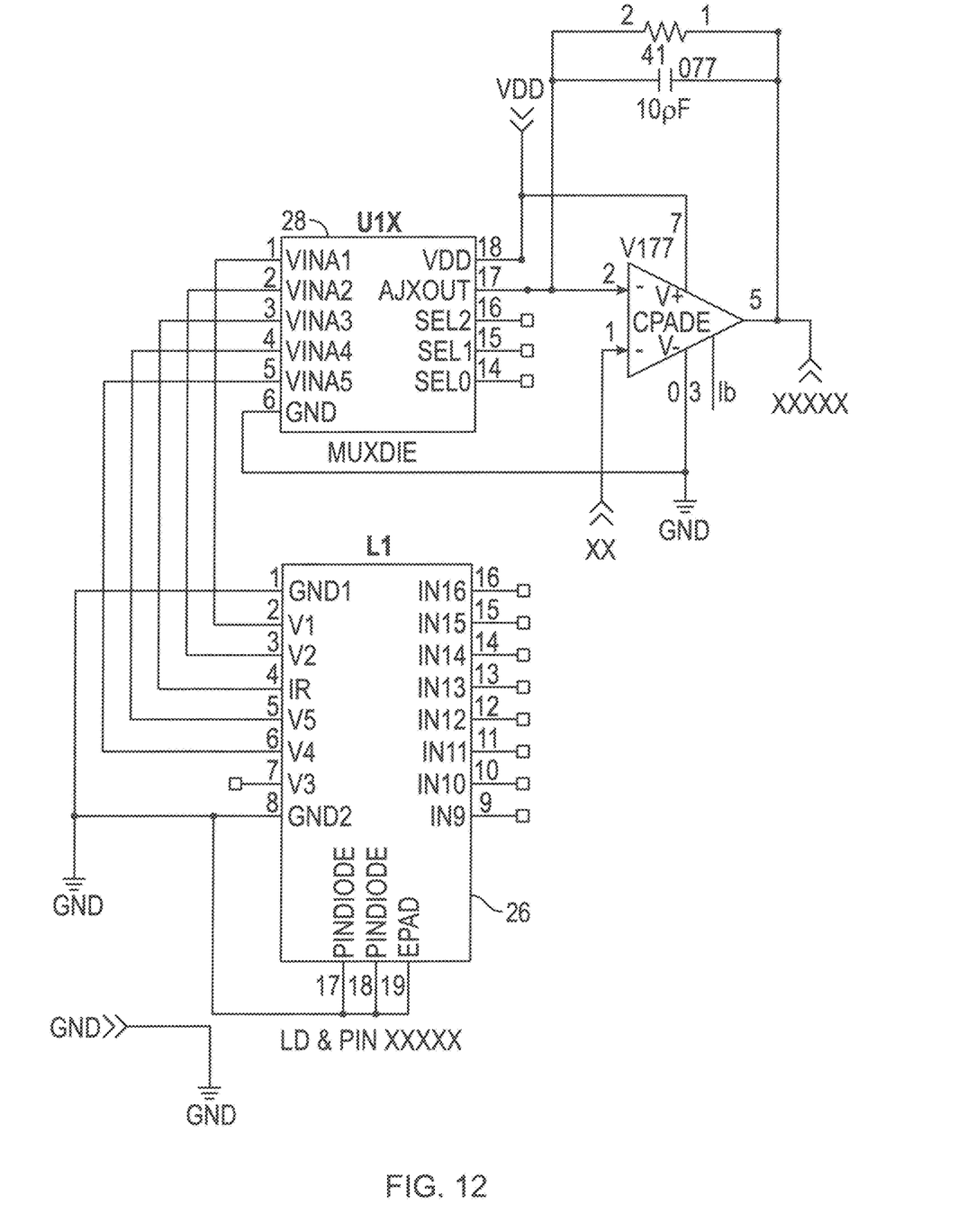
FIG. 12 is an exemplary multiplexed transconductor used in the device in accordance with one aspect of the present invention.
Figure 13:
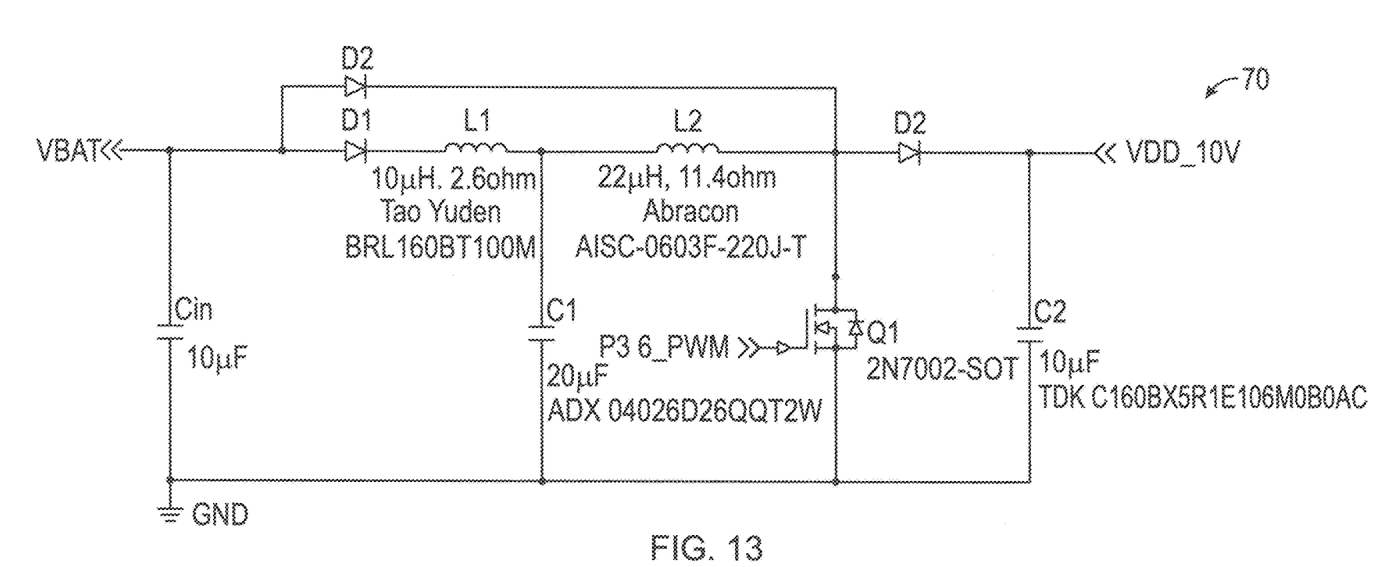
FIG. 13 is an exemplary quadratic converter used in the device in accordance with one aspect of the present invention.
Figure 15:
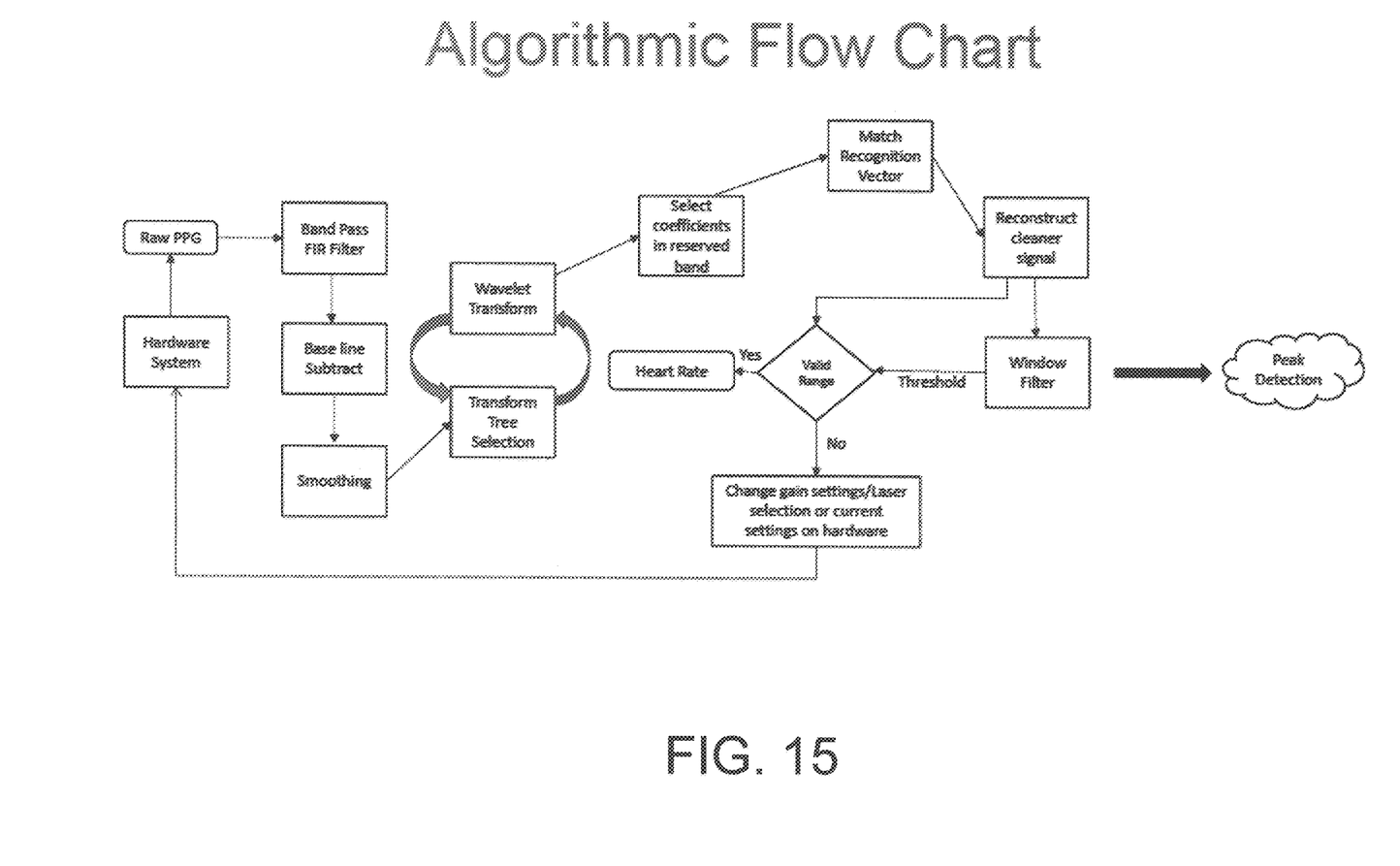
FIG. 15 is an exemplary flow chart showing operation of a processor used in the device in accordance with one aspect of the present invention.

In addition, multiple laser emitters 12 or detectors 18 might be used emitting and detecting different wavelengths. If multiple detectors 18 are used, to couple these detectors 18 to a transconductor 26, a multiplexer 28 may be used as shown in FIG. 12. The transconductor 26 may be used to generate a voltage signal proportional to the reflected light signal received. The transconductor 26 might have a programmable gain 28 or might have a fixed gain and be followed by a voltage gain device. The output of the transconductor 26 or voltage gain means might in be coupled to an A/D converter for compatibility with digital processors. Current drivers 30 may also be used which provide a programmable current source 32 for ensuring the laser emitters 12 are working in the lasing region of operation and further are producing the correct amount of light. These drivers 30 may pulse the laser emitters 12 to reduce power consumption and heat. A DC/DC converter may be included in the chip scale module to generate the power rails for the ICs and the LEDs. This DC/DC may be dynamically controlled by the processor 22 so that voltage levels are only generated when required. For example, an ARM microcontroller may need only 1.6V for general computation but must be increased to 2.4V when outputting a DAC value or reading using an ADC. A green laser may require 6V to operate but only for a short time. To minimize components sizes the DC/DC converter may utilize a quadratic converter topology 70 as shown in FIG. 13. This device 10 may be controlled by an intelligent processor 22 to implement an algorithmic methodology as shown in FIG. 15. The system may also include a frequency-based filter to bandpass the response of interest before utilizing the wavelet processing means. The overall wire bonded chip scale module might appear similar to that shown in FIG. 2.

Figure 14:
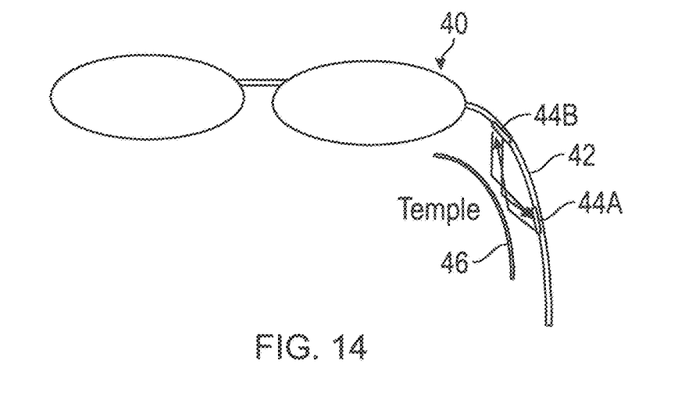
FIG. 14 is an exemplary two chip scale devices placed within a glasses frame in accordance with one aspect of the present invention.

Two or more chip scale devices may be used where the lenslet 18C directs light to the user's skin such that it may reflect from the skin and be detected by the photodetector 18A on the second module as shown in FIG. 14. For example, on the temple 42 of glasses 40, the device 10 may be formed of two modules 44A and 44B. The two modules 44A and 44B may be spaced apart such that module 44A could light up the temple 46 of the user from one side and be picked up by the module 44B or vice versa to increase the area that is illuminated and the chance of one of the lenslet beams reflecting from the skin into the other photodetector 18A is increased.

Many of the methods described in the text above may be extended to extract physiological information from animals. For example, a dog or cat collar or harness might utilize these methods to extract heart rate, diet or health related information from those animals or an ear sensor on a cow or horse might help separate sick animals from the rest of the herd by looking at their HRV and heart rate or SPO2 (stress, fatigue, sickness, blood oxygen, respiration, etc.).

The foregoing description is illustrative of particular embodiments of the application, but is not meant to be a limitation upon the practice thereof. The following claims, including all equivalents thereof, are intended to define the scope of the application.

What is claimed is:

1. A device to obtain physiological information comprising:
   at least one laser emitter;
   at least one optical detector detecting at least one of a change or difference in optical power absorption; and
   a processor;
   wherein the at least one laser emitter, the at least one optical detector, and the processor are wire bonded into a same chip scale module.

2. The device of claim 1, comprising a passive optical device directing a light from the at least one laser toward a targeted area of a user of the device, the passive optical device configured into the chip scale module.

3. The device of claim 2, wherein the passive optical device is one of a prism, cylinder or mirror.

4. The device of claim 1, wherein the at least one laser emitter is one of a VCSEL or side emitting laser.

5. The device of claim 1, comprising a lenslet, the lenslet collimates and directs light from the one or more laser emitters at one or more different angles.

6. The device of claim 1, wherein the at least one optical detector is a photodetector, the photodetector having at least one of: side blocking edging light tubes formed on the same chip scale module and directing light emitted from the at least one laser and reflected back to the photodetector.

7. The device of claim 1, comprising:
   a passive optical device directing a light om the at least one laser towards a targeted area of a user of the device; and
   side blocking edging formed around the one optical detector on the same chip scale module;
   wherein the passive optical device and side blocking edging allowing the at least one laser emitter and at least one optical detector to be co-located in a single window.

8. The device of claim 1, comprising:
   a passive optical device directing a light from the at least one laser towards a targeted area of a user of the device; and
   light tubes position above the one optical detector and on the same chip scale module directing reflected light from the targeted area to the at least one optical detector;
   wherein the passive optical device and the light tubes allowing the at least one laser emitter and at least one optical detector to be co-located in a single window.

9. The device of claim 1, wherein the device is coupled to one of eyewear, jewelry or an oral appliance.

10. The device of claim 1, wherein the at least one optical detector is a photodetector, the photodetector monitoring at least one of variations or differences in optical power reflected from the user to determine at least one of: change in blood flow, heart rate, oxygenation, blood alcohol level, keytones, glucogens and other body readings.

11. The device of claim 1, wherein the at least one optical detector comprises:
   a plurality of optical detectors, wherein the plurality of optical detectors are photodetectors; and
   a transconductor coupled to the plurality of photodetectors to generate a voltage signal proportional to a reflected light signal received.

12. The device of claim 11, comprising a multiplexer coupled to the transconductor.

13. The device of claim 11, comprising a programmable current driver coupled to the at one laser emitter.

14. The device of claim 1, comprising a transmitter wirelessly transmitting data from the device.

15. A device to obtain physiological information comprising:
   a processor,
   at least one laser emitter coupled to the processor;
   at least one optical detector detecting at least one of a change or difference in optical power absorption coupled to the processor;
   a passive optical device directing light beams from the at one laser emitter towards a target area of a user of the device; and
   a lenslet collimating and directing the light beams from the at least one laser emitters at one or more different angles towards the target area;
   wherein the at least one laser emitter, the at least one optical detector, the passive optical device, and the processor are wire bonded into a same chip scale module.

16. The device of claim 15, wherein the passive optical device is one of a prism, cylinder or mirror.

17. The device of claim 15, wherein the at least one optical detector comprises:
   a plurality of optical detectors, wherein the plurality of optical detectors are photodetectors;
   a transconductor coupled to the plurality of photodetectors to generate a voltage signal proportional to a reflected light signal received; and
   a multiplexer coupled to the transconductor.

18. The device of claim 15, wherein the at least one laser emitter is a tunable laser emitter.

19. The device of claim 15, comprising a transmitter wirelessly transmitting data from the device.

20. The device of claim 15, wherein the photodetector is one of an HgCdTe photodetector, a Micro-Opto-Electromechanical System (MOEMS) fabry-perot interferometer, or other tunable detector.

21. The device of claim 15, wherein the processor uses wavelet processing and machine learning to extract signals from noise and motion artifacts.

* * * * *